(12) United States Patent
Termanini

(10) Patent No.: US 8,114,164 B2
(45) Date of Patent: Feb. 14, 2012

(54) BICONDYLAR RESURFACING PROSTHESIS AND METHOD FOR INSERTION THROUGH DIRECT LATERAL APPROACH

(76) Inventor: Zafer Termanini, Cedar Grove, NJ (US)

( * ) Notice: Subject to any disclaimer, the term of this patent is extended or adjusted under 35 U.S.C. 154(b) by 0 days.

(21) Appl. No.: 11/715,692

(22) Filed: Mar. 8, 2007

(65) Prior Publication Data

US 2008/0119939 A1 May 22, 2008

Related U.S. Application Data

(60) Provisional application No. 60/860,409, filed on Nov. 21, 2006.

(51) Int. Cl.
*A61F 2/38* (2006.01)
(52) U.S. Cl. ................ 623/20.14; 623/20.21; 623/20.31
(58) Field of Classification Search ............... 623/20.21, 623/20.3, 20.31, 20.32, 20.35
See application file for complete search history.

(56) References Cited

U.S. PATENT DOCUMENTS

| 6,299,645 | B1 * | 10/2001 | Ogden ........................ 623/20.21 |
| 6,485,519 | B2 * | 11/2002 | Meyers et al. ............. 623/20.24 |
| 6,620,198 | B2 * | 9/2003 | Burstein et al. ............ 623/20.28 |
| 2003/0028196 | A1 * | 2/2003 | Bonutti ........................... 606/87 |
| 2003/0233149 | A1 * | 12/2003 | Hodorek .................... 623/20.35 |

* cited by examiner

*Primary Examiner* — David Isabella
*Assistant Examiner* — Joshua Levine

(57) ABSTRACT

A bicondylar implantable prosthesis resurfaces only the weight bearing portion of the patient's femur. The prosthesis includes a thin shell convexly curved outer articular surface including a medial condyle, a lateral condyle, and an intercondylar bridge, and a concave inner surface of the prosthesis that has at least one transverse ridge extending across the width of the prosthesis. When the prosthesis is implanted on the weight bearing portion of the femur, the entire outer surface of the curved articular surface is sized to resurface substantially only the weight bearing portion and no portion of the patello-femoral joint of the knee. The prosthesis is configured to be implantable by a lateral insertion through a direct lateral approach to a retropatellar region of the patient's knee joint, during which insertion the at least one transverse ridge guides the prosthesis along a laterally resected surface of the femur.

13 Claims, 8 Drawing Sheets

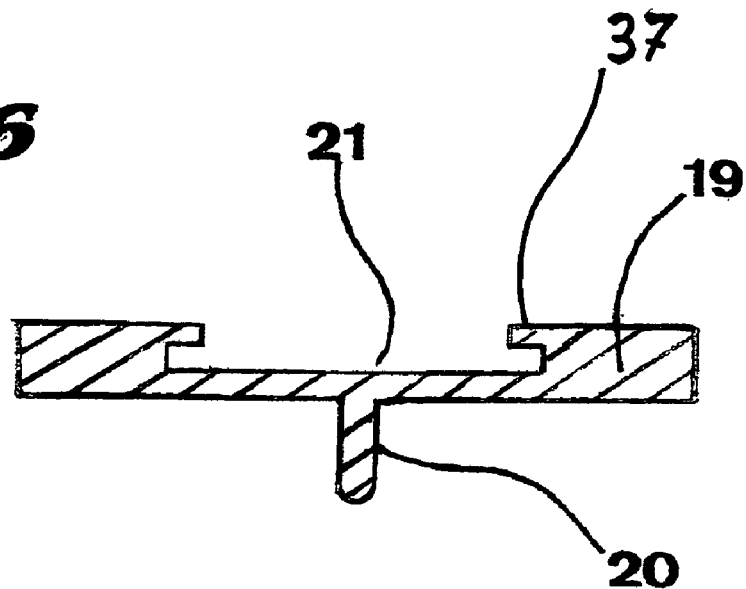
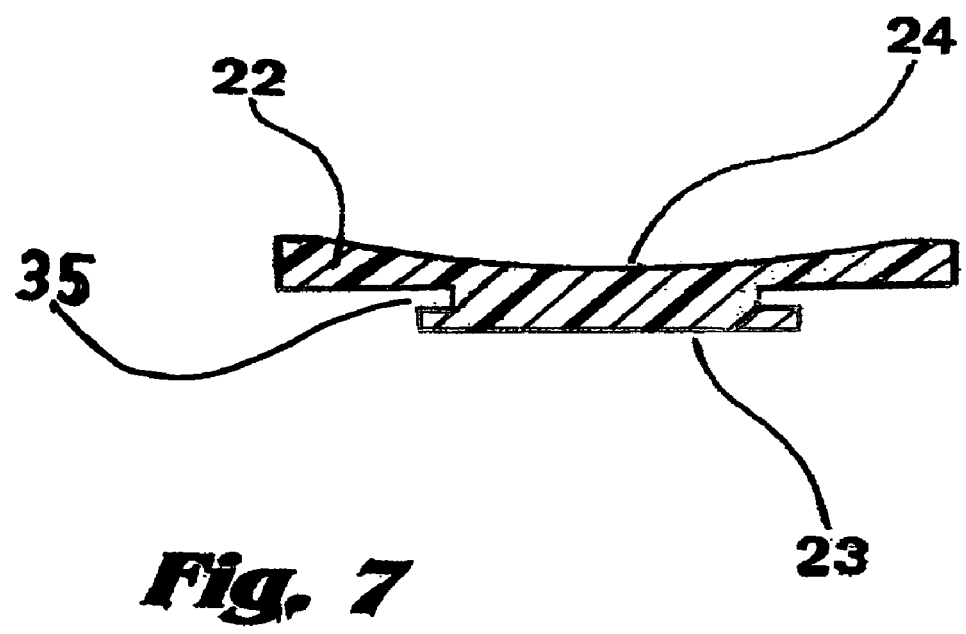

BICONDYLAR RESURFACING PROSTHESIS AND METHOD FOR INSERTION THROUGH DIRECT LATERAL APPROACH

CROSS-REFERENCE TO RELATED APPLICATIONS

This application claims priority from prior U.S. Provisional Application No. 60/860,409 filed Nov. 21, 2006. The entire disclosure of which is incorporated herein by reference.

BACKGROUND OF THE INVENTION

1. Field of the Invention

The present invention relates generally to a knee resurfacing prosthesis and more specifically it relates to a bicondylar knee resurfacing prosthesis for bicompartmental knee resurfacing, which is inserted through a limited and minimally invasive lateral approach, without any disruption of the extensor mechanism or damage to the quadriceps tendon.

2. Description of the Related Art

It can be appreciated that knee-resurfacing prostheses have been in use for years to treat articular surfaces destroyed by arthritis or pathological processes secondary to trauma. Basically, the natural knee joint comprises an upper femoral articular surface having two condylar surfaces and a lower tibial plateau comprising two cupules shaped tibial condyles articulating smoothly with the upper femoral condyles. Typically, knee replacement prostheses are comprised of several types of prostheses, where articular compartments of the knee are removed and replaced with metal and polyethylene components.

The devices of prior art attempted to duplicate the geometry of the natural articular surface, where the femoral component have a semicircular C shaped device such as depicted in a U.S. Pat. No. 4,224,696. The bicondylar design is similarly disclosed in prior patents by F. Buechel and Pappas in U.S. Pat. Nos. 4,309,778 and 4,470,158. More recent bicondylar design is described in U.S. Pat. No. D473,307S and U.S. Pat. No. 6,197,064 B1. The prior art describes the bicondylar prosthesis as having a middle patellar groove for the femoral patellar articulation. Other knee resurfacing devices are used to resurface only one femoral condyle such as unicondylar prostheses described in U.S. Pat. No. 7,141,053; U.S. U.S. Pat. No. 6,726,724B2, Most unicondylar devices used septum, pegs and alike for fixation. The unicondylar design as described in U.S. Pat. No. 6,299,645 B1 used multiple dovetail pegs for fixation to one femoral condyle.

However, unicondylar prostheses in general present a high rate of failure due to loosening and dislocation secondary to poor distribution of weight and high concentration of stress over a small surface. Furthermore, almost all the patents cited above described prostheses that are inserted through a conventional anterior, anteromedial or anterolateral surgical approach.

The main problem with conventional knee resurfacing prostheses is the fact that the surgical approach used during their insertion causes extensive soft tissue disruption and irreparable scarring to major anatomical structures. Another problem with conventional knee resurfacing prostheses is the anterior surgical approach that violates the extensor mechanism of the knee joint, namely, the quadriceps muscle, quadriceps tendon and the medial extensor retinaculum. Another problem with conventional knee resurfacing prostheses is the need to laterally dislocate and "flip over" the patella and the patellar tendon in order to access both condyles, which frequently weakens the insertion of the patellar tendon, causing undue pain in the immediate post operative period.

While these devices may be suitable for the particular purpose to which they address, they are, because of their size, not suitable for bicondylar knee resurfacing through a limited lateral approach, without disrupting the extensor mechanism or damaging the quadriceps tendon. The main problem with conventional knee resurfacing prostheses is the fact that both condyles are approached anteriorly through a medial or lateral para patellar approach, which causes extensive soft tissue disruption and irreparable scarring to major anatomical structures by violating the extensor mechanism of the knee joint, namely, the quadriceps muscle and tendon.

Another problem is the large size of the femoral component of the conventional prosthesis, which makes it very difficult to insert through a limited true lateral approach that is appropriately described for the prosthesis of this invention. The prosthesis of this invention is thinner and much smaller than the conventional total knee femoral component, since it does not address the femoro-patellar joint.

In these respects, the bicondylar knee resurfacing prosthesis according to the present invention substantially departs from the conventional concepts and designs of the prior art, and in so doing provides an apparatus primarily developed for the purpose of resurfacing the articular surfaces of the femur and the tibia through a limited and true lateral approach, without disruption of the extensor mechanism or damage to the quadriceps tendon. Furthermore, the prosthesis of the present invention does not address the patello femoral joint such as other conventional devices and hence, is much thinner and smaller in size.

SUMMARY OF THE INVENTION

In view of the foregoing disadvantages inherent in the known types of knee resurfacing prostheses now present in the prior art, the present invention provides a new bicondylar knee resurfacing prosthesis construction wherein the same can be utilized for a bicondylar knee resurfacing procedure inserted through a small direct lateral approach, without disruption of the extensor mechanism or damage to the quadriceps tendon.

The general purpose of the present invention, which will be described subsequently in greater detail, is to provide a new bicondylar knee resurfacing prosthesis that has many of the advantages of the knee resurfacing prosthesis mentioned heretofore and many novel features that result in a new mini bicondylar knee resurfacing prosthesis which is not anticipated, rendered obvious, suggested, or even implied by any of the prior art knee resurfacing prosthesis, either alone or in any combination thereof.

To attain this, the present invention generally comprises a metallic femoral component retaining the anatomical geometry, reduced in size to match the weight-bearing portion of both femoral condyles, a metallic tibial tray and a polyethylene tibial insert.

The metallic femoral component has a curved arcuate polished convex articular surface in a form of two condyles, medial and lateral, which are connected together by an intercondylar bridge. The concave surface has a femoral fixation means in the form of a straight metallic transverse ridge. Said ridge has the shape of a dovetail in its cross-section and extends along the entire width of the femoral component. Said component has a thickness between 2 millimeters at its thinner posterior condylar region and 6 millimeters at the thickest weight-bearing portion. In addition, the concave surfaces can also be cemented using conventional methylmethacrylate bone cement.

A metallic tibial tray, which will be inserted laterally through a mini incision in the lateral quadrilateral space delineated in FIG. 1, has a bottom surface to be affixed to the tibial plateau. Said bottom surface has a fixation means in the form of a dovetail retaining ridge. Said dovetail fixation means extends transversely along the entire width of the metallic tray. The top surface provides a transverse recess in a form of dovetail retaining groove to hold the polyethylene tibial insert. Said dovetail retaining groove is positioned transversely along the entire width of the metallic tibial tray so that the polyethylene tray can be slidingly inserted laterally through a mini incision in the quadrilateral space.

Once slid into position in the tibial dovetail groove, the polyethylene insert will be firmly retained by a locking mechanism comprising a small recess in the metallic tibial tray and a corresponding protruding tang provided at the bottom of the polyethylene tray. This will allow the polyethylene component to lock in place after complete insertion and prevents it from moving out once it is locked in.

[There has thus been outlined, rather broadly, the more important features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a bicondylar knee resurfacing prosthesis for a bicondylar knee resurfacing that is limited to the weight-bearing and the arc of motion area between the tibia and the femur, which is inserted through a limited lateral direct approach, situated within the lateral quadrilateral space and without disruption of the extensor mechanism or damage to the quadriceps tendon. It provides a bicondylar knee resurfacing prosthesis that will overcome the shortcomings of the prior art devices.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

FIG. 6 is a cross-sectional view of the tibial metallic component.

FIG. 7 is a cross-sectional view of the polyethylene insert.

DETAILED DESCRIPTION OF THE INVENTION AND PREFERRED EMBODIMENT

Figure 1:
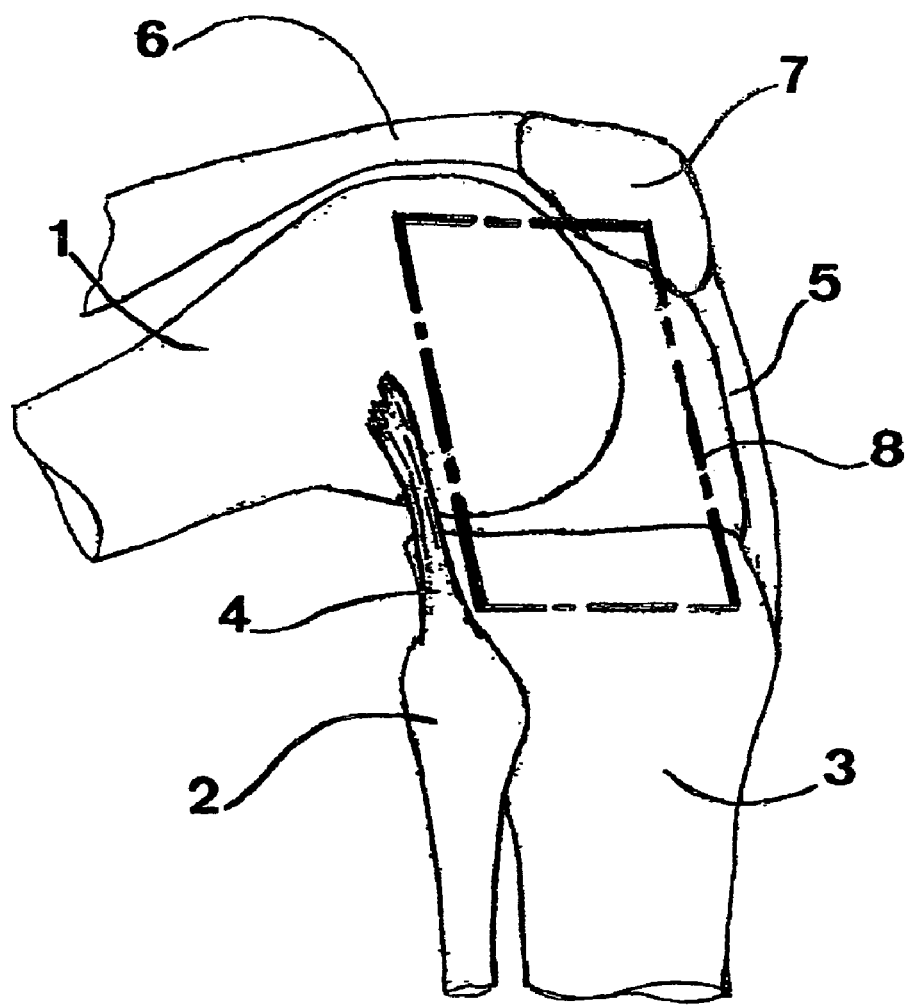
FIG. 1 is a side view of the normal bony anatomical structures of the knee joint in full flexion revealing the quadrilateral space.
Figure 2:
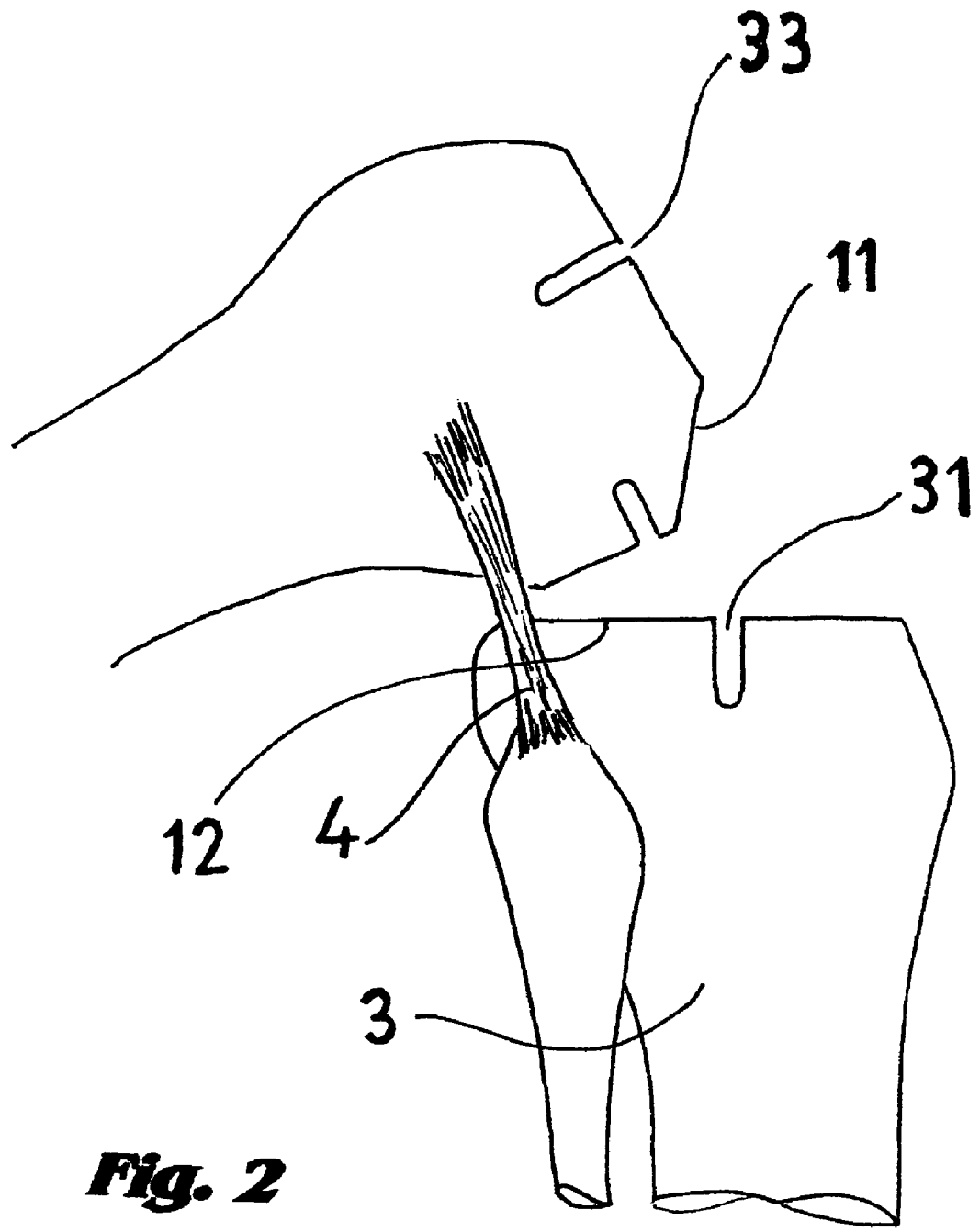
FIG. 2 is a side view of the normal bony structures of the knee joint flexion after preparation of the femoral and tibial articular surfaces and burring the dovetail grooves.

Turning now descriptively to the drawings, in which similar reference characters denote similar elements throughout the several views, the attached figures illustrate a concise bicondylar knee resurfacing prosthesis, which comprises a thin metallic femoral arcuate component, a metallic tibial tray and a polyethylene tibial insert.

An arcuate metallic femoral component has a polished convex articular surface in a form of two condyles, medial 28 and lateral 25, that are connected with an intercondylar bridge 16.

The preferred embodiment of the present invention is a concise thin shell like bicondylar metallic arcuate component having a thickness between 2 millimeters at its thinner posterior condylar region 18 and 6 millimeters at the thickest weight bearing portion 17.

Figure 4:
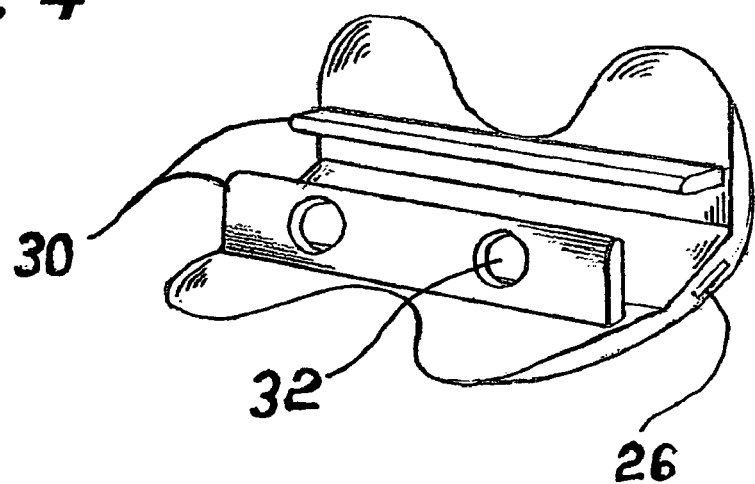
FIG. 4 is an antero lateral view of the femoral component exposing the transverse dovetail retaining ridge.
Figure 3:
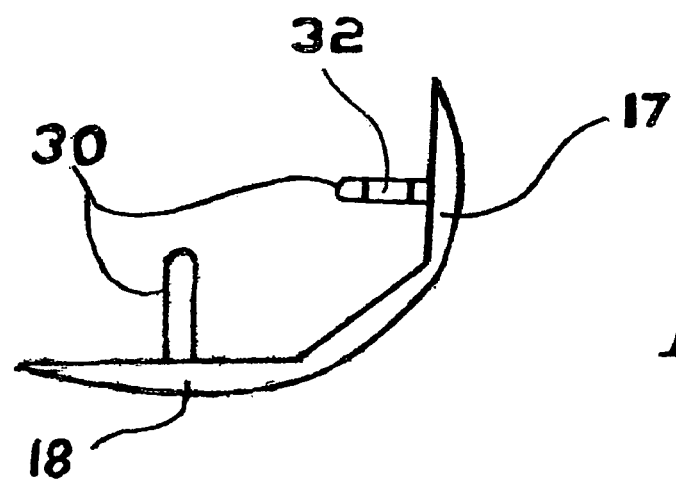
FIG. 3 is a side view of the femoral metallic prosthetic component revealing the retaining dovetail ridge.
Figure 5:
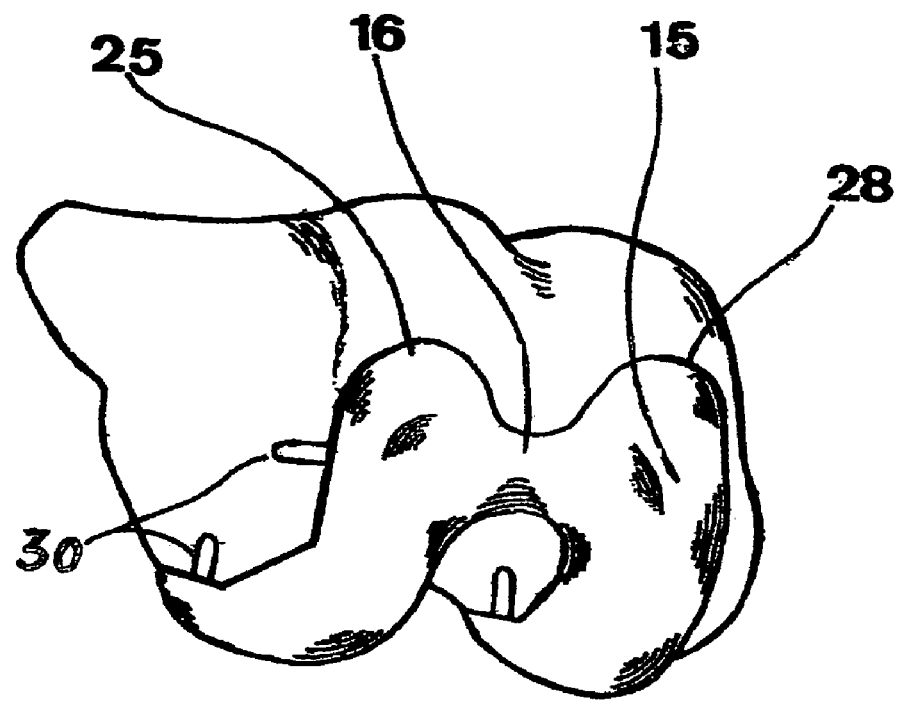
FIG. 5 is an antero lateral view of the femoral component inserted onto the femur.
Figure 8:
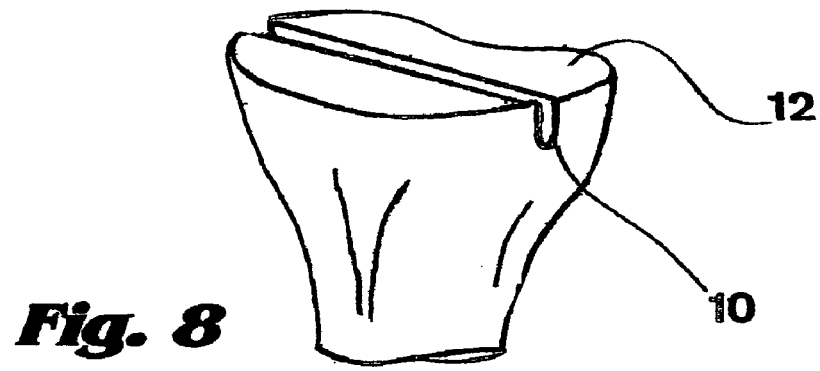
FIG. 8 is an anteromedial view of the resected tibial plateau showing the tibial dovetail retaining groove ready to receive the tibial metallic tray.

The concave surface has a metallic transverse ridge 14. Said ridge has the shape of a dovetail in its section and extends along the entire width of the femoral component, as depicted in FIG. 4. Said dovetail retaining ridge has 20° angles between the two-sloped sides.

The height of the septum ridge is approximately 12 millimeters, and measures approximately 5 millimeters at its narrow base in contact with the body of the femoral component. At the outer or lateral end of the dovetail ridge, an orifice 26 allows the attachment of insertion tools.

In another preferred embodiment of the present invention, the angle between the two sloped sides of the dovetail ridge is reduced to zero degrees, so that said sloped surfaces become parallel and subsequently the dovetail ridge becomes a fin like transverse ridge. More than one perpendicular fin can be provided in order to increase the stability of the femoral component.

The concave surface provides fine asperities and voids to allow bone ingrowth, which will solidly affix the femoral metallic component to bone. Said femoral metallic component can also, if need arise, be cemented to the femur using conventional methyl methacrylate bone cement.

Figure 9:
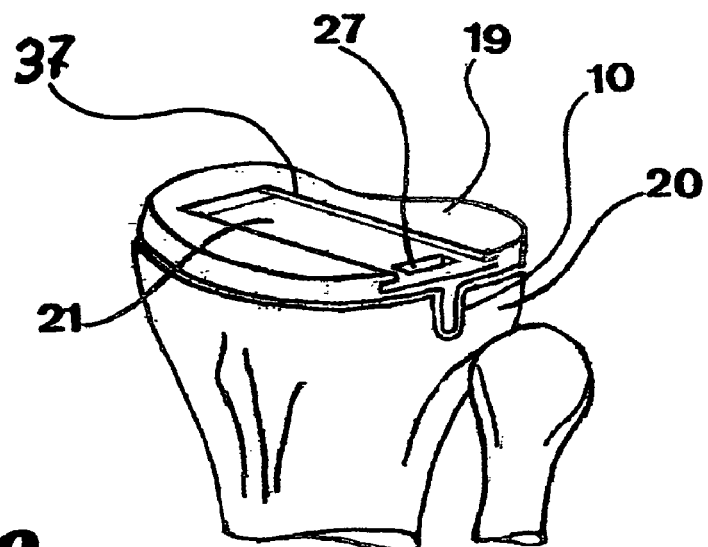
FIG. 9 is an anteromedial view of the tibial plateau showing the metallic tibial tray inserted in place.

A metallic tibial tray 19 having a flat top and bottom surfaces. As shown in FIG. 6, the top surface provides a recess 21 in the form of a dovetail for the purpose of securely retaining the polyethylene tibial insert. Said dovetail recess runs transversely across the entire flat width of the metallic tibial tray and stops one quarter of an inch short of the medial edge of the metallic tibial tray, as shown in FIG. 9.

The bottom surface of the metallic tray, which is in contact with tibial plateau, has a metallic ridge 20 having the shape of a dovetail, which runs transversely across the entire width of the bottom surface of the metallic tibial tray, as shown in FIG. 6.

The height of the ridge is approximately 12 millimeters, and measures approximately 5 millimeters at its narrow base in contact with the body of the tibial component. Said dovetail ridge has 20° angles between the two sloped sides. The tibial tray may or may not be cemented to the tibia using conventional bone cement.

In another preferred embodiment of the present invention, the angle between the two sloped sides of the dovetail ridge is reduced to zero degrees, so that said sloped surfaces become parallel and subsequently the dovetail ridge becomes a fin-like transverse ridge. More than one perpendicular fin can be provided in order to increase the fixation and the stability of the component.

The tibial insert 22 is made of polyethylene and has the same shape and size of the tibial metallic tray as shown in FIG. 7. The top surface, which articulates with the femoral component, provides two cupules or shallow condylar grooves 24 that conformably match the condylar convex surfaces of the metallic femoral medial and lateral condyles, as shown in FIG. 10.

Figure 10:
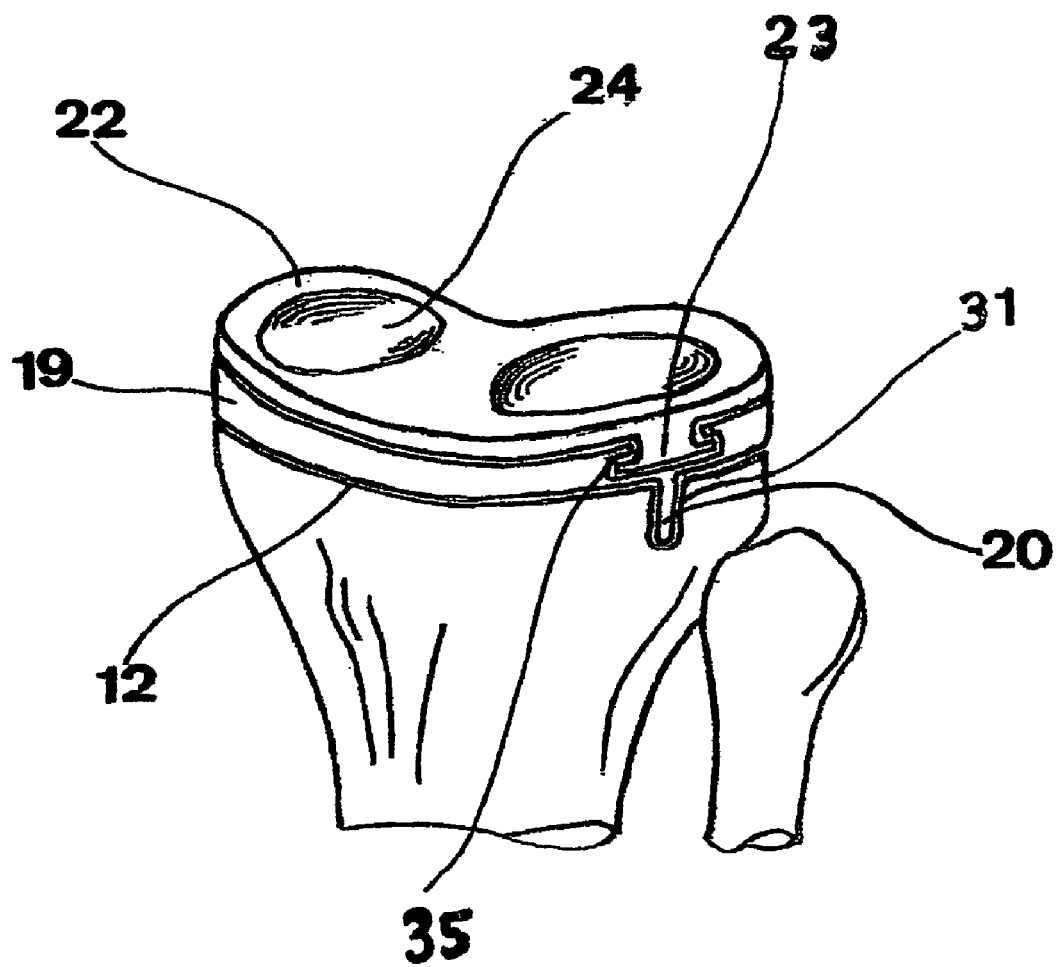
FIG. 10 is an anteromedial view of the tibial plateau showing the metallic tibial tray and the polyethylene tibial tray inserted in place into their correspondent dovetail grooves.
Figure 11:
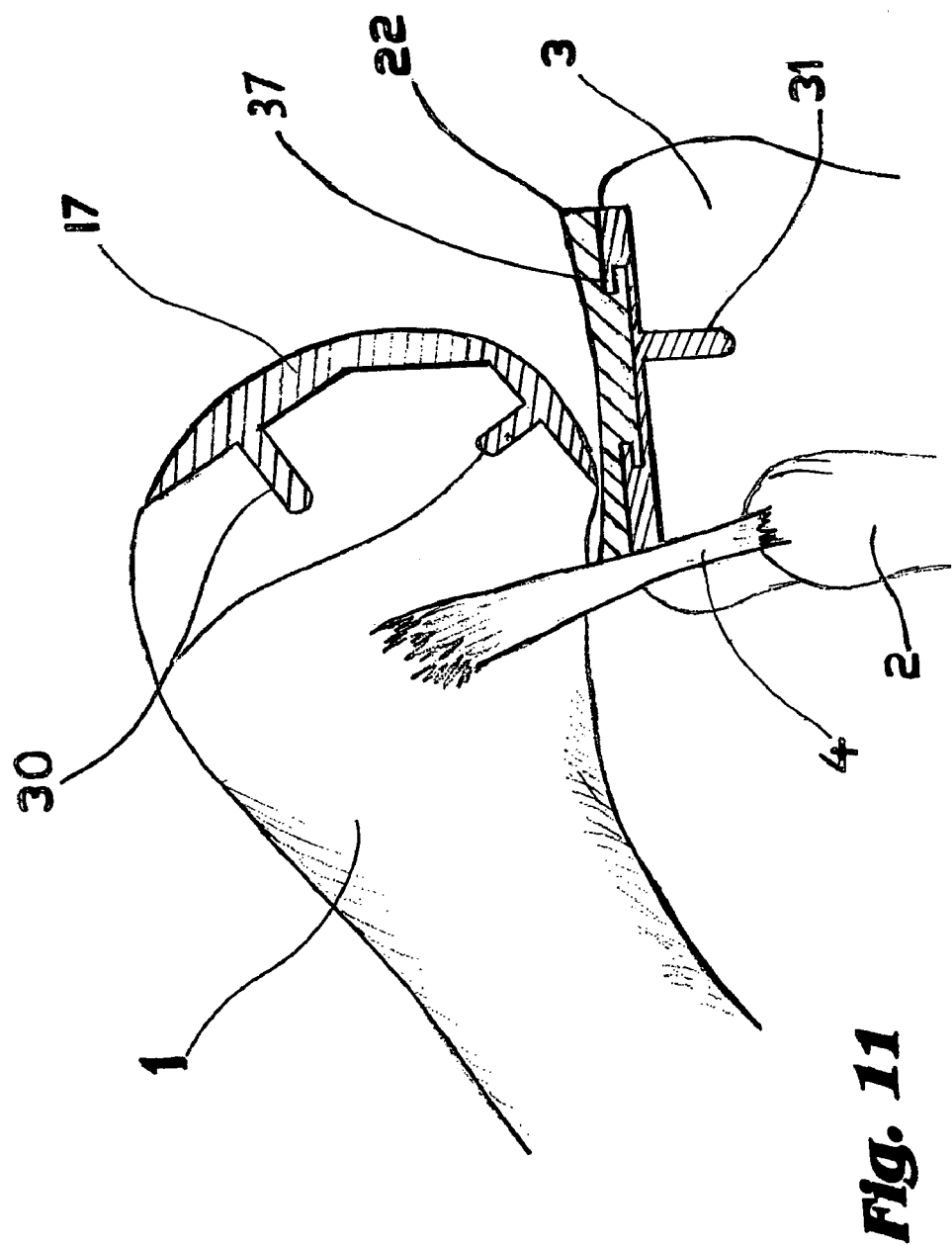
FIG. 11 is a side view of the femoral metallic component, polyethylene insert, and tibial metallic component inserted in place.

The bottom surface of said polyethylene tibial insert having a dove tail configuration 23 that runs transversely and can slide conformably and easily into the corresponding top groove 21 of the metallic tibial tray as shown in FIG. 10.

In addition, the tibial insert has a locking mechanism in a form of a small lateral recess 27, situated at the lateral end of the dovetail groove 21, which will receive a small locking tab extending from the inferior surface of the polyethylene insert, locking it in place after insertion and preventing it from moving out once its it locked in, as shown in FIG. 10.

Initially, the knee joint is approached through a very limited lateral incision in the lateral quadrilateral space as shown in FIG. 1. The retropatellar region is approached directly and the infrapatellar fat pad is excised. Care is taken to avoid injury to the lateral collateral ligament, which is retracted posteriorly. The placement of appropriate jigs and cutting guides is facilitated by the use of computerized navigation systems, which aid in appropriate positioning of the instrumentation based on digital extrapolation from the patient's knee CT scan. In view of the concise approach and limited incision, it is needless to state that the precise shaving and dovetail burring of the bone is greatly facilitated by the use of a robot interfaced to a conventional navigation system.

Total condylar resurfacing is made possible using the above-described technique and approaching the knee joint through a direct mini lateral approach. The approach is safe, noninvasive and spares the extensor mechanism and the quadriceps tendon. This will undoubtedly reduce the postoperative pain and provide a sooner return to normal activity.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A bicondylar implantable prosthesis for resurfacing only the weight bearing portion of the patient's femur being defined by the articular surface of the femur that contacts the patient's tibia during flexing from full extension through flexion, the prosthesis comprising:
    a thin shell convexly curved outer articular surface including a medial condyle, a lateral condyle, and an intercondylar bridge; and
    a concave inner surface of the prosthesis that has at least one transverse ridge extending across a width of the prosthesis,
    wherein, when the prosthesis is implanted on the weight bearing portion of the femur, the entire outer surface of the curved articular surface is sized to resurface substantially only the weight bearing portion and no portion of the patello-femoral joint of the knee, and
    wherein the prosthesis is configured to be implantable by a lateral insertion through a direct lateral approach to a retropatellar region of the patient's knee joint, during which insertion the at least one transverse ridge guides the prosthesis along a laterally resected surface of the femur.

2. The prosthesis of claim 1, wherein the at least one transverse ridge includes two planar sides extending from the inner surface,
    wherein the two planar sides are substantially parallel to the direction of the lateral insertion, and
    wherein the two planar sides are substantially parallel to each other.

3. The prosthesis of claim 2, wherein the inner surface has more than one transverse ridge.

4. The prosthesis of claim 3, wherein the inner surface has two transverse ridges.

5. An implantable prosthetic device for forming a joint between a patient's femur and tibia, comprising:
    a bicondylar femoral component having a curved articular portion including a medial condyle, a lateral condyle, and an intercondylar bridge, an inner surface of the femoral component including at least one femoral transverse ridge;
    a tibial platform having a bottom surface, which includes at least one tibial transverse ridge, and a top surface, which includes at least two restraining lips; and
    a polyethylene insert having a top surface, which includes two condylar grooves, and a bottom surface, which includes a transverse retaining ridge,
    wherein, when the femoral component is implanted on the femur, no portion of the outer surface of the prosthesis resurfaces any area of the patello-femoral joint,
    wherein the femoral component is implantable by a first lateral insertion through a direct lateral approach to a retropatellar region of the patient's knee joint, during which insertion the at least one femoral transverse ridge guides the femoral component along a laterally resected surface of the femur, wherein the tibial platform is implantable by a second lateral insertion through the direct lateral approach to the retropatellar region, during which insertion the at least one tibial transverse ridge guides the tibial platform along a laterally resected surface of the tibia, and wherein the polyethylene insert is implantable by a third lateral insertion through the direct lateral approach to the retropatellar region, during which insertion the transverse retaining ridge contacts the tibial platform and guides the insert along the restraining lips of the top surface of the tibial platform.

6. The prosthetic device of claim 5, wherein the at least one femoral transverse ridge includes two planar sides extending from the inner surface, wherein the two planar sides are substantially parallel to the direction of the lateral insertion, and wherein the two planar sides are substantially parallel to each other.

7. The prosthetic device of claim 6, wherein the inner surface of the femoral component has more than one transverse ridge.

8. The prosthetic device of claim 7, wherein the inner surface of the femoral component has two transverse ridges.

9. The prosthetic device of claim 5, wherein the inner surface of the femoral component includes fine asperities and voids.

10. A method for forming a joint between a patient's femur and tibia, comprising:

establishing a direct lateral approach to a retropatellar region of the patient's knee joint;

laterally resecting a surface of the femur;

laterally resecting a surface of the tibia;

laterally inserting through the direct lateral approach an implantable bicondylar femoral prosthesis having a curved articular portion that includes a medial condyle, a lateral condyle, and an intercondylar bridge, the femoral prosthesis having an inner surface with at least one transverse ridge, such that when the prosthesis is implanted on the femur, no portion of the outer surface of the prosthesis resurfaces any area of the patello-femoral joint;

laterally inserting through the direct lateral approach an implantable tibial prosthesis including a platform having a bottom surface, which includes at least one transverse ridge, and a top surface, which includes at least two restraining lips; and laterally inserting through the direct lateral approach a polyethylene insert having a bottom surface, which includes a transverse retaining ridge.

11. A method for resurfacing a patient's femur, comprising:

establishing a direct lateral approach to a retropatellar region of the patient's knee joint;

laterally resecting a surface of the femur; and laterally inserting through the direct lateral approach an implantable femoral prosthesis according to claim 1.

12. The prosthesis of claim 1, wherein the at least one transverse ridge is located at least partially on the intercondylar bridge.

13. The prosthesis of claim 2, wherein an angle between the at least one transverse ridge and the inner surface of the prosthesis is 75° or greater and 105° or less.

* * * * *